United States Patent
Ueda et al.

(10) Patent No.: US 10,281,417 B2
(45) Date of Patent: May 7, 2019

(54) TIRE CHARACTERISTIC VALUE MEASUREMENT APPARATUS AND TIRE CHARACTERISTIC VALUE MEASUREMENT SYSTEM

(71) Applicant: MITSUBISHI HEAVY INDUSTRIES MACHINERY SYSTEMS, LTD., Hyogo (JP)

(72) Inventors: Tatsuya Ueda, Hiroshima (JP); Yasutaka Seimoto, Hiroshima (JP)

(73) Assignee: MITSUBISHI HEAVY INDUSTRIES MACHINERY SYSTEMS, LTD., Kobe-shi, Hyogo (JP)

( * ) Notice: Subject to any disclaimer, the term of this patent is extended or adjusted under 35 U.S.C. 154(b) by 0 days.

(21) Appl. No.: 15/545,544

(22) PCT Filed: Aug. 3, 2016

(86) PCT No.: PCT/JP2016/072732
§ 371 (c)(1),
(2) Date: Jul. 21, 2017

(87) PCT Pub. No.: WO2017/110128
PCT Pub. Date: Jun. 29, 2017

(65) Prior Publication Data
US 2018/0011041 A1    Jan. 11, 2018

(30) Foreign Application Priority Data

Dec. 24, 2015  (JP) .................................. 2015-251002

(51) Int. Cl.
*G01M 17/02* (2006.01)
*G01N 27/04* (2006.01)
*G01M 1/14* (2006.01)

(52) U.S. Cl.
CPC ............ *G01N 27/041* (2013.01); *G01M 1/14* (2013.01); *G01M 17/02* (2013.01); *G01M 17/021* (2013.01)

(58) Field of Classification Search
CPC .............................. G01N 27/041; G01M 17/02
(Continued)

(56) References Cited

U.S. PATENT DOCUMENTS 4,488,430 A    12/1984  Fujimoto et al.
6,178,814 B1 *  1/2001  Curtis ................. G01M 17/021
                                                    73/146

(Continued)

FOREIGN PATENT DOCUMENTS

CN    104053999 A    9/2014
JP    S58-008630 A    1/1983
(Continued)

OTHER PUBLICATIONS

PCT/ISA/210, "International Search Report for International Application No. PCT/JP2016/072732," dated Oct. 18, 2016.
(Continued)

*Primary Examiner* — Reena Aurora
(74) *Attorney, Agent, or Firm* — Manabu Kanesaka; Benjamin Hauptman; Kenneth Berner

(57) ABSTRACT

A tire characteristic value measurement apparatus (100) includes a support arm (124) which is provided in vertical movement means (111 to 121). The support arm (124) bears a tire (T) on a roller conveyor (101) from below and has electrically insulative properties. The tire characteristic value measurement apparatus (100) further includes electric resistance value detection means (125 to 139) which is provided in the vertical movement means (111 to 121). The
(Continued)

electric resistance value detection means (125 to 139) detects an electric resistance value of the tire T borne by the support arm (124).

8 Claims, 9 Drawing Sheets

(58) Field of Classification Search
USPC .......................................................... 324/722
See application file for complete search history.

(56) References Cited

U.S. PATENT DOCUMENTS

| | | | |
|---|---|---|---|
| 2002/0166372 A1 | 11/2002 | Farne | |
| 2009/0072842 A1 | 3/2009 | Murakami et al. | |
| 2013/0247657 A1* | 9/2013 | Sumitani | G01M 17/021 73/146 |
| 2014/0303908 A1* | 10/2014 | Sotgiu | G01B 21/32 702/41 |
| 2015/0241491 A1 | 8/2015 | Ueda et al. | |

FOREIGN PATENT DOCUMENTS

| | | |
|---|---|---|
| JP | S61-033547 Y2 | 10/1986 |
| JP | 2000-009771 A | 1/2000 |
| JP | 2006-317380 A | 11/2006 |
| JP | 4146155 B2 | 9/2008 |
| JP | 4150108 B2 | 9/2008 |
| JP | 2008-247068 A | 10/2008 |
| JP | 2012-185117 A | 9/2012 |
| JP | 2014-089161 A | 5/2014 |
| WO | 2014/069039 A1 | 5/2014 |

OTHER PUBLICATIONS

PCT/ISA/237 "Written Opinion of the International Searching Authority for International Application No. PCT/JP2016/072732," dated Oct. 18, 2016.

* cited by examiner

TIRE CHARACTERISTIC VALUE MEASUREMENT APPARATUS AND TIRE CHARACTERISTIC VALUE MEASUREMENT SYSTEM

RELATED APPLICATIONS

The present application is National Phase of International Application No. PCT/JP2016/072732 filed Aug. 3, 2016, and claims priority from Japanese Application No. 2015-251002, filed Dec. 24, 2015, the disclosure of which is hereby incorporated by reference herein in its entirety.

TECHNICAL FIELD

The present invention relates to a tire characteristic value measurement apparatus measuring a characteristic value such as an electric resistance value of a tire, and a tire characteristic value measurement system.

Priority is claimed on Japanese Patent Application No. 2015-251002, filed on Dec. 24, 2015, the content of which is incorporated herein by reference.

BACKGROUND ART

In a tire of an automobile or the like, when a vehicle body is electrified, an electric resistance value is adjusted within a regulated range such that an electric charge can be diverted to the ground surface. Therefore, tire manufacturing factories utilize an apparatus measuring the electric resistance value of a manufactured tire on a manufacturing line.

As such an apparatus measuring the electric resistance value of a tire, for example, as disclosed in PTL 1, an apparatus has been proposed. The apparatus measures the electric resistance value of a tire by causing a pair of probes to rise from below a roller conveyor with respect to the tire which has been conveyed on the roller conveyor and to interpose the tire therebetween.

CITATION LIST

Patent Literature

[PTL 1] Japanese Unexamined Patent Application Publication No. 2014-089161
[PTL 2] Japanese Unexamined Patent Application Publication No. 2006-317380
[PTL 3] Japanese Unexamined Patent Application Publication No. 2000-009771

SUMMARY OF INVENTION

Technical Problem

In an apparatus proposed in PTL 1, in a state where a tire is in contact with a roller of a metal roller conveyor, an electric resistance value of the tire is measured. Therefore, depending on various types of conditions such as the size and the structure of a tire, it is difficult to measure the electric resistance value of the tire with high accuracy in some cases.

For example, it is possible to consider applying a roller conveyor formed of an insulative material such as resin. However, when the roller conveyor is applied to conveying a tire which is heavy in weight, a disadvantage is caused in durability, thereby being not practical.

An object of the present invention is to provide a tire characteristic value measurement apparatus in which measuring a characteristic value such as an electric resistance value of a tire can be easily executed with high accuracy, and a tire characteristic value measurement system.

Solution to Problem

According to a first aspect of the present invention, there is provided a tire characteristic value measurement apparatus including conveyance means for conveying a tire, vertical movement means which is installed below the conveyance means and is able to vertically move. The tire characteristic value measurement apparatus also includes a bearing member which is provided in the vertical movement means and bears the tire on the conveyance means from below in accordance with a rise, and in which at least a contact surface with respect to the tire has electrically insulative properties. The tire characteristic value measurement apparatus also includes electric resistance value detection means which is provided in the vertical movement means and detects an electric resistance value of the tire borne by the bearing member.

According to a second aspect of the present invention, the tire characteristic value measurement apparatus of the first aspect may further include weight detection means which is provided in the vertical movement means and detects a weight of the tire borne by the bearing member.

According to a third aspect of the present invention, the vertical movement means of the tire characteristic value measurement apparatus of the second aspect may include a fluid pressure cylinder which is installed such that an axial direction is oriented toward an upward/downward direction. The vertical movement means may also include an offset support member of which a base end portion is coupled to an upper end of the fluid pressure cylinder and of which a tip end portion is positioned at a position offset to the side lower than the upper end of the fluid pressure cylinder when the fluid pressure cylinder contracts. The vertical movement means may also include guide means which is coupled to the offset support member and guides a vertical movement of the offset support member. The weight detection means and the electric resistance value detection means may be supported by the tip end portion of the offset support member of the vertical movement means. The bearing member may be provided in the weight detection means.

According to a fourth aspect of the present invention, the guide means of the vertical movement means of the third aspect may also include a pair of guide rails of which a longitudinal direction is oriented toward the upward/downward direction. The guide means may also include sliders which are respectively provided in the guide rails so as to be able to slide along the longitudinal direction of the guide rails and are individually coupled to the offset support member.

According to a fifth aspect of the present invention, the electric resistance value detection means of any one aspect of the third aspect and the fourth aspect may also include probes which make a pair. The electric resistance value detection means may also include probe holding means which is supported by the tip end portion of the offset support member of the vertical movement means and holds the probes making a pair such that the probes are able to move in a direction of approaching and being separated from each other.

According to a sixth aspect of the present invention, the tire characteristic value measurement apparatus of any one aspect from the second aspect to the fifth aspect may further include a weight measurement station which has a weight/electric resistance measurement portion having the electric resistance value detection means and the weight detection means, and a tire marking portion being able to perform marking on the tire, and in which the tire marking portion is disposed above the weight/electric resistance measurement portion.

According to a seventh aspect of the present invention, the weight measurement apparatus of the sixth aspect may also include a center position adjustment mechanism which adjusts a center position of the tire. The center position adjustment mechanism may also include a rotary position adjustment roller which abuts a part of the tire and is rotated so as to rotate the tire around an axis line of the tire.

According to an eighth aspect of the present invention, there is provided a tire characteristic value measurement system including the tire characteristic value measurement apparatus of the sixth or seventh aspect, and a uniformity machine which is disposed on an upstream side of the weight measurement station in a conveyance direction of the tire and measures uniformity of the tire. The tire characteristic value measurement system also includes a dynamic balancing machine which is disposed on an upstream side of the weight measurement station in the conveyance direction of the tire and measures an amount of imbalance in the tire. The tire marking portion individually marks a measurement result of the uniformity machine and a measurement result of the dynamic balancing machine on the tire.

Advantageous Effects of Invention

According to the tire characteristic value measurement apparatus, measuring the electric resistance value of a tire can be easily executed with high accuracy.

DESCRIPTION OF EMBODIMENTS

Embodiments of a tire characteristic value measurement apparatus according to the present invention will be described based on the drawings. However, the present invention is not limited to the following embodiments described based on the drawings.

First Embodiment

A first embodiment of the tire characteristic value measurement apparatus according to the present invention will be described based on FIGS. 1 to 3.

Figure 1:
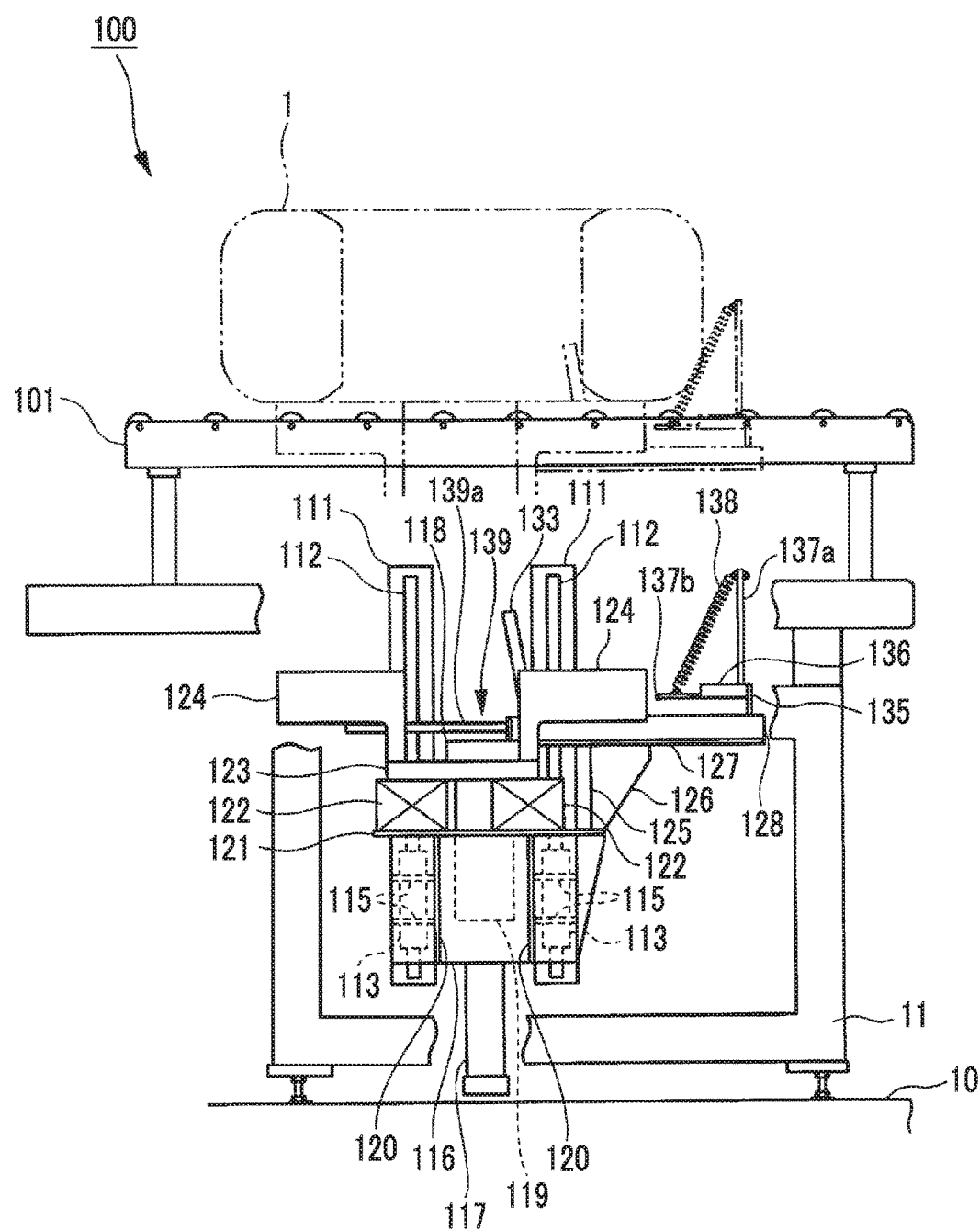
FIG. 1 is a side view illustrating a schematic structure of the main portion of a tire characteristic value measurement apparatus according to a first embodiment of the present invention.

FIG. 1 is a side view illustrating a schematic structure of the main portion of a tire characteristic value measurement apparatus according to a first embodiment of the present invention. FIG. 2 is a front view illustrating the schematic structure of the main portion of the tire characteristic value measurement apparatus according to the first embodiment of the present invention. FIG. 3 is a plan view illustrating the schematic structure of the main portion of the tire characteristic value measurement apparatus according to the first embodiment of the present invention.

Figure 2:
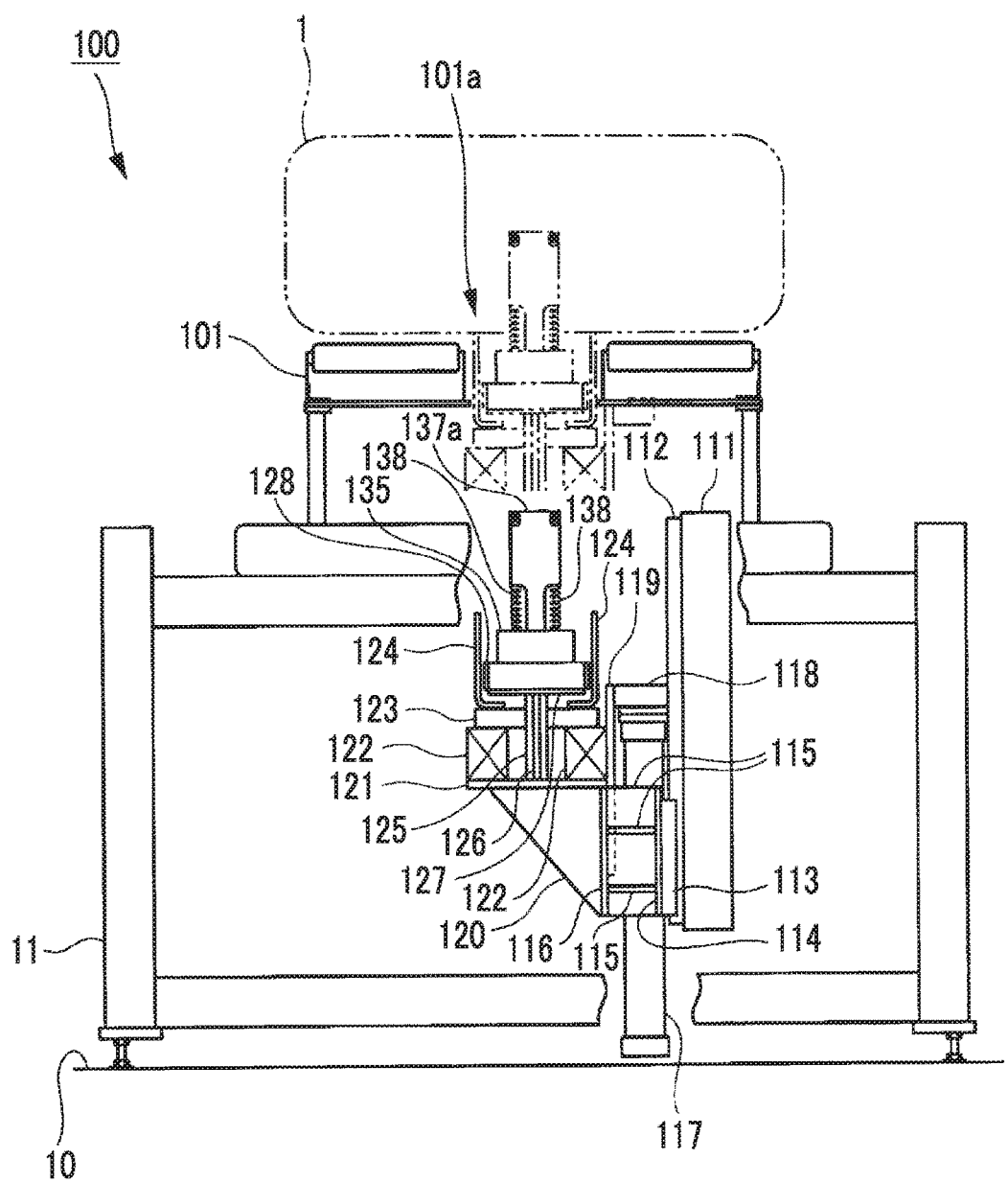
FIG. 2 is a front view illustrating the schematic structure of the main portion of the tire characteristic value measurement apparatus according to the first embodiment of the present invention.

As illustrated in FIGS. 1 and 2, on a main body frame 11 installed on a floor surface 10, a metal roller conveyor 101 which is conveyance means for conveying a tire T is attached.

Figure 3:
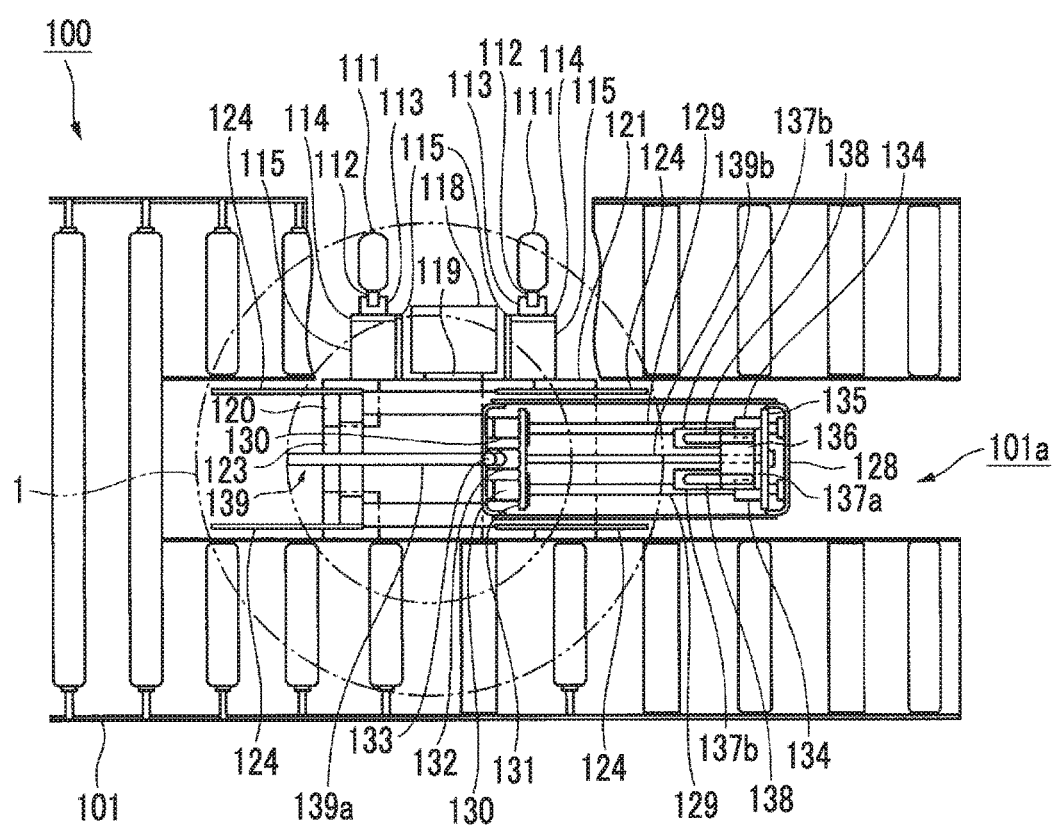
FIG. 3 is a plan view illustrating the schematic structure of the main portion of the tire characteristic value measurement apparatus according to the first embodiment of the present invention.

As illustrated in FIG. 3, the roller conveyor 101 is formed lengthily in a conveyance direction (in FIG. 3, transverse direction) in the middle in the width direction (in FIG. 3, upward/downward direction) and includes an advance/retreat slit 101a causing upper and lower portions to communicate with each other.

As illustrated in FIGS. 1 to 3, on one side in the width direction below the roller conveyor 101 (depth direction of the sheet in FIG. 1, rightward direction in FIG. 2, and upward direction in FIG. 3), columns 111 supported with respect to the main body frame 11 are provided such that the longitudinal direction is oriented toward the upward/downward direction. There are provided two columns 111 making a pair in the conveyance direction of the roller conveyor 101 (transverse direction in FIG. 1, perpendicular direction of the sheet in FIG. 2, and transverse direction in FIG. 3).

In the columns 111 making a pair, guide rails 112 are respectively attached to surfaces on the advance/retreat slit 101a side of the roller conveyor 101 (front direction of the sheet in FIG. 1, left side in FIG. 2, and lower side in FIG. 3) so as to make a pair. The longitudinal direction of the guide rails 112 is oriented toward the longitudinal direction (upward/downward direction) of the columns 111.

In the guide rails 112 making a pair, sliders 113 which can slide in the longitudinal direction of the guide rails 112 are respectively attached.

In the sliders 113, attachment plates 114 are respectively attached to surfaces on the advance/retreat slit 101a side of the roller conveyor 101 (front direction of the sheet in FIG. 1, left side in FIG. 2, and lower side in FIG. 3).

In the attachment plates 114, coupling plates 116 are respectively attached to surfaces on the advance/retreat slit 101a side of the roller conveyor 101 (front direction of the sheet in FIG. 1, left side in FIG. 2, and lower side in FIG. 3). The coupling plates 116 cause the sliders 113 of the guide rails 112 making a pair to be coupled to each other. The coupling plates 116 are respectively attached to the attachment plates 114 via brackets 115.

An air cylinder 117 is provided between the guide rails 112 making a pair. The air cylinder 117 is a fluid pressure cylinder and is supported by the main body frame 11. The air cylinder 117 is disposed such that the tip end of a rod thereof is oriented upward and is disposed such that an axial direction thereof is oriented toward the upward/downward direction. An attachment plate 118 is attached to the tip end (upper end) of the rod of the air cylinder 117.

In the attachment plate 118, the upper end side (one end side) of a support plate 119 is coupled to an end portion on the advance/retreat slit 101a side of the roller conveyor 101 thereof (front direction of the sheet in FIG. 1, left side in FIG. 2, and lower side in FIG. 3). The support plate 119 is disposed so as to be parallel to the coupling plates 116 such that the longitudinal direction thereof is oriented toward the upward/downward direction.

A portion of the support plate 119 on a lower side of the middle in the upward/downward direction thereof (to the other end) is fixed to the coupling plates 116. In the coupling plates 116, a support table 121 is supported on surfaces on the advance/retreat slit 101a side of the roller conveyor 101 thereof (front direction of the sheet in FIG. 1, left side in FIG. 2, and lower side in FIG. 3) via a bracket 120. The support table 121 is positioned below the advance/retreat slit 101a of the roller conveyor 101 and is disposed such that the longitudinal direction is oriented toward the horizontal direction.

That is, when the rod of the air cylinder 117 protrudes and retracts, the coupling plates 116 can be lifted and lowered via the attachment plate 118 and the support plate 119, and the support table 121 can vertically move via the bracket 120. Moreover, when the rod of the air cylinder 117 protrudes and retracts, the sliders 113 slide along the guide rails 112 via the brackets 115 and the attachment plates 114. Accordingly, a vertical movement of the support table 121 can be guided so as to be stable.

A plurality of load cells 122 is disposed on the support table 121. On the plurality of load cells 122, a support frame 123 is attached. The support frame 123 is attached so as to straddle the plurality of load cells 122. Support arms 124 stand on the support frame 123. The support arms 124 stand such that the longitudinal direction thereof is oriented toward the conveyance direction of the roller conveyor 101 (longitudinal direction of the advance/retreat slit 101a). The support arms 124 are formed of electrically insulative materials such as plastic and ceramic and have plate shapes. There are provided four support arms 124. The four support arms 124 are provided so as to make a pair in the width direction of the roller conveyor 101 (transverse direction in FIG. 2 and upward/downward direction in FIG. 3) and to make a pair in the conveyance direction of the roller conveyor 101 (transverse direction in FIG. 1 and transverse direction in FIG. 3).

That is, when the rod of the air cylinder 117 protrudes and the support table 121 moves upward, the support arms 124 can move upward beyond the roller conveyor 101 through the advance/retreat slit 101a of the roller conveyor 101 via the load cells 122 and the support frame 123. When the rod of the air cylinder 117 retracts and the support table 121 is lowered, the support arms 124 can move downward beyond the roller conveyor 101 through the advance/retreat slit 101a of the roller conveyor 101 via the load cells 122 and the support frame 123.

A strut 125 stands on the support table 121. The strut 125 is provided on a side close to a first end portion of the support table 121 (a side close to the right end in FIGS. 1 and 3) in the conveyance direction of the roller conveyor 101 (longitudinal direction of the advance/retreat slit 101a). The upper end of the strut 125 is coupled to a lower surface of a base plate 127. The base plate 127 is supported on the support table 121 via the strut 125 and a bracket 126.

On the base plate 127, a frame body 128 is attached. The frame body 128 is provided along the circumferential edge of the base plate 127. Two guide rods 129 are installed inside the frame body 128. The two guide rods 129 are provided so as to make a pair with a gap therebetween in the width direction of the roller conveyor 101, respectively in postures such that the axial direction is oriented toward the conveyance direction of the roller conveyor 101. Both end sides of the guide rods 129 are individually fixed to the frame body 128.

Slide blocks 130 are respectively attached to the two guide rods 129. The slide blocks 130 are disposed on a side close to the first end portions of the guide rods 129 (left side in FIG. 3). The slide blocks 130 are attached so as to be respectively slidable with respect to the two guide rods 129. The slide blocks 130 are integrally coupled to each other by a coupling plate 131. A support member 132 is attached to the coupling plate 131. The support member 132 supports a rod-type probe 133. In an erected posture, the lower end of the probe 133 is supported by the support member 132.

That is, the probe 133 can slide in the axial direction of the guide rods 129 via the support member 132, the coupling plate 131, and the slide blocks 130.

Moreover, slide blocks 134 are respectively provided in the guide rods 129. The slide blocks 134 are disposed on a side close to second end portions of the guide rods 129 (right side in FIG. 3). The slide blocks 134 are attached so as to be respectively slidable with respect to the guide rods 129. The slide blocks 134 are integrally coupled to each other by a coupling plate 135. A base end portion of a support member 136 (right end in FIGS. 1 and 3) is attached to the upper end portion of the coupling plate 135.

In the support member 136, a vertical frame 137a stands on an upper surface on a side close to the base end portion thereof (right end in FIGS. 1 and 3). The vertical frame 137a stands in a posture in which the longitudinal direction thereof is oriented toward the upward/downward direction. Transverse frames 137b are coupled to the support member 136.

In the transverse frames 137b, base end portions thereof (right end in FIGS. 1 and 3) are fixed to the end surface (left end surface in FIGS. 1 and 3) of the tip end portion of the support member 136 in a posture in which the longitudinal direction thereof is oriented toward the horizontal direction. There are provided two transverse frames 137b making a pair in the width direction of the roller conveyor 101 (upward/downward direction in FIG. 3).

The lower end portions (end portions on one side) of probes 138 are respectively coupled to the tip end portions (left side in FIGS. 1 and 3) of the transverse frames 137b. The upper end portions (end portions on the other side) of the probes 138 are respectively coupled to the upper end portion of the vertical frame 137a. The probes 138 are coil spring-type probes making a pair.

That is, the probes 138 can slide along the guide rods 129 via the vertical frame 137a, the transverse frames 137b, the support member 136, the coupling plate 135, and the slide blocks 134.

In the coupling plate 131, the tip end of an outer tube 139a of an air cylinder 139 is coupled to a surface on the first end portion side (left side in FIGS. 1 and 3) in the conveyance direction of the roller conveyor 101. The air cylinder 139 is a fluid pressure cylinder provided in a posture in which the longitudinal direction is oriented toward the conveyance direction of the roller conveyor 101. The outer tube 139a of the air cylinder 139 penetrates the frame body 128 on the first end portion side (left side in FIGS. 1 and 3) in the conveyance direction of the roller conveyor 101 and is supported by the frame body 128 so as to be slidable in the axial direction.

An inner rod 139b of the air cylinder 139 has a tip end penetrating the coupling plate 131 and is coupled to the coupling plate 131.

That is, when the inner rod 139b of the air cylinder 139 retracts, the coupling plates 131 and 135 can slide so as to approach each other in the axial direction of the guide rods 129. In accordance with the sliding of the coupling plates 131 and 135 approaching each other, the probes 133 and 138 can approach each other so as to narrow the distance between the probes 133 and 138. When the air cylinder 139 is stretched, the coupling plates 131 and 135 can slide so as to be separated from each other in the axial direction of the guide rods 129. In accordance with the sliding of the coupling plates 131 and 135 being separated from each other, the probes 133 and 138 can be separated from each other so as to widen the distance between the probes 133 and 138.

Figure 4:
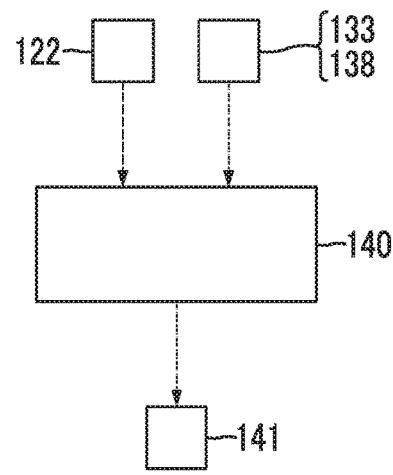
FIG. 4 is a block diagram of the main portion of the tire characteristic value measurement apparatus in FIGS. 1 to 3.

FIG. 4 is a block diagram of the main portion of the tire characteristic value measurement apparatus in FIGS. 1 to 3.

As illustrated in FIG. 4, the load cells 122 and the probes 133 and 138 are electrically connected to a calculation control device 140 which is calculation control means. The calculation control device 140 measures weights added onto the support arms 124, based on information from the load cells 122. Moreover, the calculation control device 140 can measure an electric resistance value between the probes 133 and 138 based on information from the probes 133 and 138 (for details, refer to PTL 1). Moreover, the calculation control device 140 can cause a display 141 which is display means such as a monitor electrically connected to an output portion, to display the measured weights, the measured electric resistance value, and the like.

In the first embodiment, the columns 111, the guide rails 112, the sliders 113, the attachment plates 114, the brackets 115, the coupling plates 116, and the like configure guide means. The attachment plate 118 serving as the base end portion, the support plate 119, the bracket 120, the support table 121 serving as the tip end portion, and the like configure an offset support member. The air cylinder 117, the guide means, the offset support member, and the like configure vertical movement means. The load cells 122 and the like configure weight detection means. The support frame 123, the support arms 124, and the like configure a bearing member. The strut 125, the bracket 126, the base plate 127, the frame body 128, the guide rods 129, the slide blocks 130 and 134, the coupling plates 131 and 135, the support members 132 and 136, the frames 137a and 137b, the air cylinder 139, and the like configure probe holding means. The probes 133 and 138, the probe holding means, and the like configure electric resistance value detection means.

In a tire characteristic value measurement apparatus 100 according to the first embodiment, the roller conveyor 101 conveys the tire T such that the tire T is positioned on the advance/retreat slit 101a. Then, the rod of the air cylinder 117 protrudes. As described above, the support table 121 moves upward, and the support arms 124 advance upward beyond the roller conveyor 101 through the advance/retreat slit 101a of the roller conveyor 101 and move to an operation position. Accordingly, the support arms 124 lift the tire T from below such that the tire T is separated from the roller conveyor 101, and the support arms 124 bear the tire T.

At this time, the weight of the tire T is added to the load cells 122 via the support arms 124 and the support frame 123, and the load cells 122 detect the amount of the increased weight. The calculation control device 140 calculates the weight of the tire T based on information from the load cells 122 and causes the display 141 to display the measurement result.

In accordance with the upward movement of the support table 121, the guide rods 129 also move upward via the strut 125, the bracket 126, the base plate 127, and the frame body 128. The probe 133 protrudes upward beyond the roller conveyor 101 through the advance/retreat slit 101a of the roller conveyor 101 via the slide blocks 130, the coupling plate 131, and the support member 132, and the probe 133 is positioned at the operation position on the inner circumferential side of the tire T. Moreover, the probes 138 move upward beyond the roller conveyor 101 through the advance/retreat slit 101a of the roller conveyor 101 via the slide blocks 134, the coupling plate 135, the support member 136, and the frames 137a and 137b, and the probes 138 are positioned at the operation position on the outer circumferential side of the tire T.

In this state, when the inner rod 139b of the air cylinder 139 retracts, the coupling plates 131 and 135 slide so as to approach each other as described above. The probe 133 abuts the inner circumference of the tire T, and the probes 138 abut the outer circumference of the tire T.

The calculation control device 140 detects the electric resistance value of the tire T based on information from the probes 133 and 138 (for details, refer to PTL 1) and causes the display 141 to display the measurement result thereof.

At this time, the support arms 124 formed of electrically insulative materials such as plastic and ceramic lift the tire T from below so as to separate the tire T from a roller of the metal roller conveyor 101, and the support arms 124 bear the tire T. Therefore, without being influenced by various types of conditions such as the size and the structure of the tire T, it is possible to easily and promptly detect the electric resistance value of the tire T and measure the same with high accuracy.

When the weight and the electric resistance value of the tire T are measured, the inner rod 139b of the air cylinder 139 protrudes, and the coupling plates 131 and 135 slide so as to be separated from each other, as described above. Then, the probe 133 is separated from the inner circumference of the tire T, and the probes 138 are separated from the outer circumference of the tire T.

Subsequently, the inner rod 139b of the air cylinder 117 retracts, and the support table 121 moves downward, as described above. Then, the support arms 124 is buried below the roller conveyor 101 through the advance/retreat slit 101a of the roller conveyor 101 and is positioned at an initial retreat position. Accordingly, the tire T is placed on the roller conveyor 101. At the same time, the probes 133 and 138 also moves downward beyond the roller conveyor 101 through the advance/retreat slit 101a of the roller conveyor 101 and returns to the initial retreat position.

After the roller conveyor 101 conveys the tire T such that the tire T shifts to a next step from the position on the advance/retreat slit 101a, a next tire T is conveyed so as to be newly positioned on the advance/retreat slit 101a.

By repeating the step described above, measuring the weight together with the electric resistance value of the tire T can be continuously executed.

According to the tire characteristic value measurement apparatus 100 of the first embodiment, measuring a characteristic value such as the electric resistance value of the tire T can be easily executed with high accuracy.

The weight of the tire T can also be measured at the same time as measuring the electric resistance value of the tire T. Therefore, since there is no need to separately provide a space and a step only for measuring the weight, it is possible to realize space-saving and short-period processing.

the tire T is borne via the support frame 123 and the support arms 124 and the weight of the tire T is measured by the load cells 122. Accordingly, a load other than the weight of the tire T added to the load cells 122 can be restrained to the minimum requirement. Therefore, the detection performance (resolution) of the load cells 122 can be enhanced, and the weight of the tire T can also be measured with high accuracy.

The attachment plate 118 serving as the base end portion is attached to the tip end (upper end) of the rod of the air cylinder 117. Moreover, the support table 121 is attached to the attachment plate 118 via the support plate 119 and the bracket 120 such that the support table 121 serving as the tip end portion is positioned at a position offset to the side lower than the tip end (upper end) of the air cylinder 117 when the air cylinder 117 contracts. Therefore, the height position of the support arms 124, the probes 133 and 138, and the like can be lowered when the support arms 124, the probes 133 and 138, and the like are positioned at the retreat position below the roller conveyor 101. As a result, it is possible to ensure a space for additionally installing other instruments below the roller conveyor 101.

Modification Example of First Embodiment

In the first embodiment, vertical movements of the support table 121 and the like are guided by attaching the guide rails 112 along the standing columns 111 and providing sliders in the guide rails 112 in a slidable manner. However, for example, a vertical movement of an offset support member may be guided by providing a sleeve in a standing guide rod in a slidable manner.

In the first embodiment, the air cylinders 117 and 139 are applied as the fluid pressure cylinder. However, in place of the air cylinders 117 and 139, for example, hydraulic cylinders or electric cylinders can be applied.

In the first embodiment, the support arms 124 formed of electrically insulative materials are applied. However, for example, it is possible to apply a support arm or the like in which only the upper surface is coated with an electrically insulative material such as plastic and ceramic. That is, the bearing member is acceptable as long as at least a contact surface with respect to the tire T is formed of a material having electrically insulative properties.

In the first embodiment, both the load cells 122 and the probes 133 and 138 are electrically connected to the calculation control device 140. However, for example, the load cells 122 and the probes 133 and 138 can be respectively and electrically connected to separate calculation control devices.

Second Embodiment

A second embodiment according to the present invention will be described based on the drawings. In the second embodiment, a tire marking apparatus and the like are further added to the first embodiment described above. Thus, description will be given by applying the same reference signs to the same portions as the first embodiment, and the overlapping description will be omitted.

Figure 5:
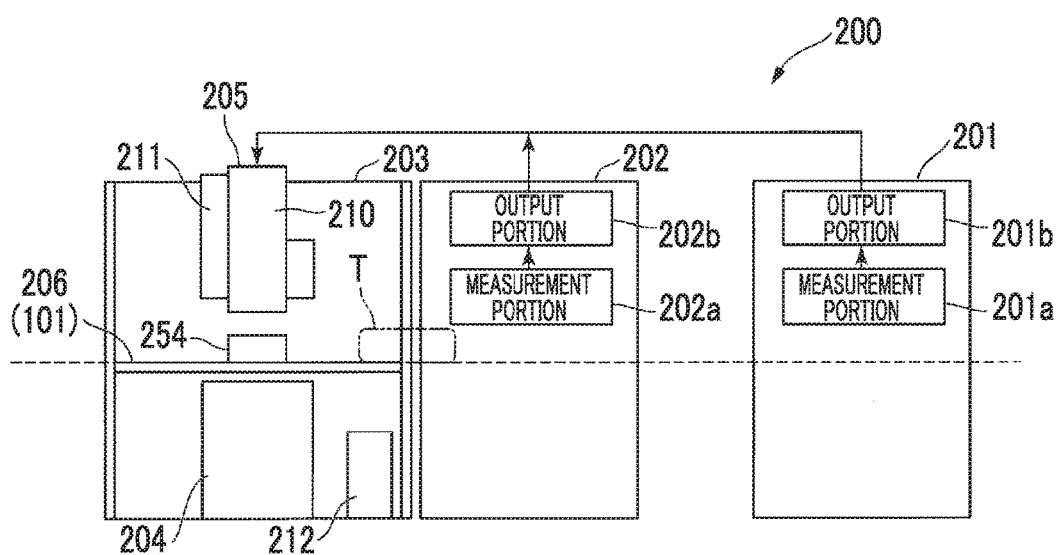
FIG. 5 is a side view illustrating a schematic configuration of a tire characteristic value measurement apparatus according to a second embodiment of the present invention.

FIG. 5 is a side view illustrating a schematic configuration of a tire characteristic value measurement apparatus according to a second embodiment of the present invention.

As illustrated in FIG. 5, a tire characteristic value measurement apparatus 200 of the second embodiment includes a tire uniformity machine 201, a dynamic balancing machine 202, and a weight measurement station 203.

The tire uniformity machine 201 measures ununiformity of a vulcanized tire T. The tire uniformity machine 201 includes a measurement portion 201a and an output portion 201b.

The measurement portion 201a measures the uniformity of the tire T in a traveling state while the tire is rotated in a state of being mounted on a pseudo rim (not illustrated) and being pressed against a load wheel (not illustrated).

The output portion 201b transmits data of a measurement result obtained by the measurement portion 201a to a tire marking portion 205 (will be described later).

The tire uniformity machine 201 according to the second embodiment carries out the tire T measured by the measurement portion 201a toward the dynamic balancing machine 202, by using a conveyance apparatus such as a roller conveyor.

The dynamic balancing machine 202 measures imbalance of a vulcanized tire T. The dynamic balancing machine 202 includes a measurement portion 202a and an output portion 202b.

The measurement portion 202a causes the tire T conveyed from the dynamic balancing machine 202 to rotate on its axis in a state of being mounted on the pseudo rim (not illustrated). Moreover, the measurement portion 202a picks up the oscillation of a rotary shaft (not illustrated) caused by the centrifugal force of the tire T, thereby converting the static amount of imbalance of the tire T itself into the dynamic amount of imbalance.

The output portion 202b transmits data of a measurement result obtained by the measurement portion 202a to the tire marking portion 205 (will be described later).

The dynamic balancing machine 202 according to the second embodiment carries out the tire T measured by the measurement portion 202a toward the weight measurement station 203, by using a conveyance apparatus such as a roller conveyor.

The weight measurement station 203 individually measures the weight and the electric resistance of the tire T as the tire characteristic value of the tire T conveyed from the dynamic balancing machine 202. Regarding the configuration of measuring the weight and the electric resistance of the tire T, the weight measurement station 203 has the same configuration as the tire characteristic value measurement apparatus 100 of the first embodiment.

The weight measurement station 203 according to the second embodiment includes a weight/electric resistance measurement portion 204, the tire marking portion 205, and a conveyance portion 206. Here, since the weight/electric resistance measurement portion 204 has a configuration similar to that of the mechanism included in the tire characteristic value measurement apparatus 100 according to the first embodiment measuring the weight and the electric resistance of the tire T, the detailed description will be omitted.

Figure 6:
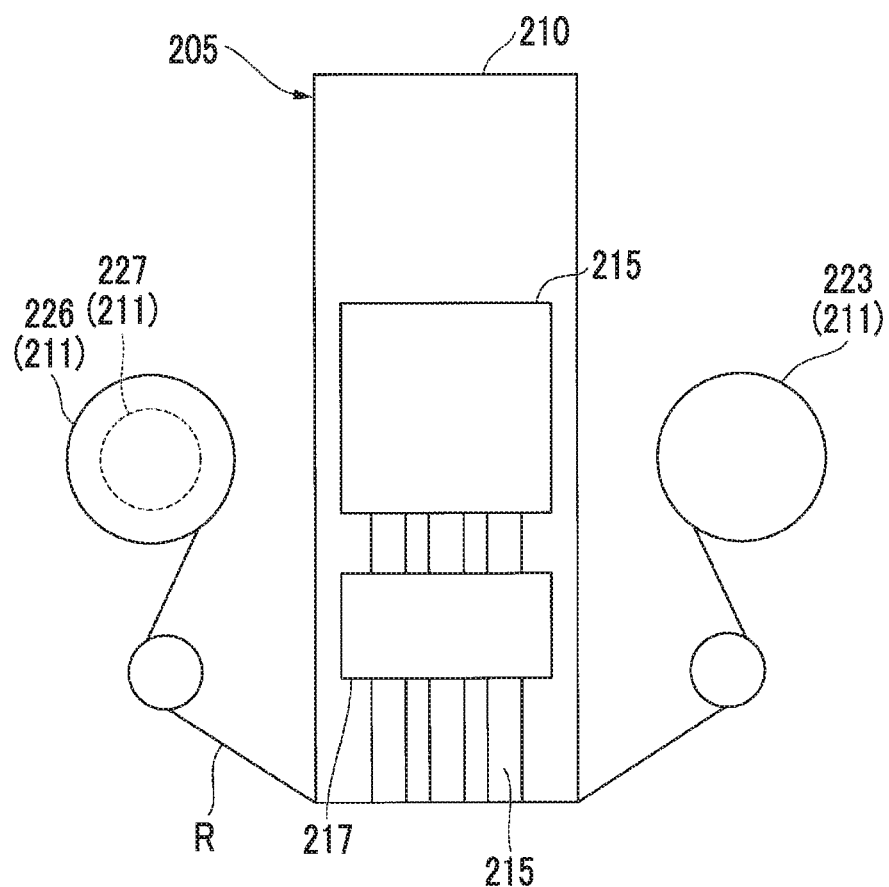
FIG. 6 is a front view illustrating a schematic configuration of a tire marking apparatus of the tire characteristic value measurement apparatus according to the second embodiment of the present invention.
Figure 7:
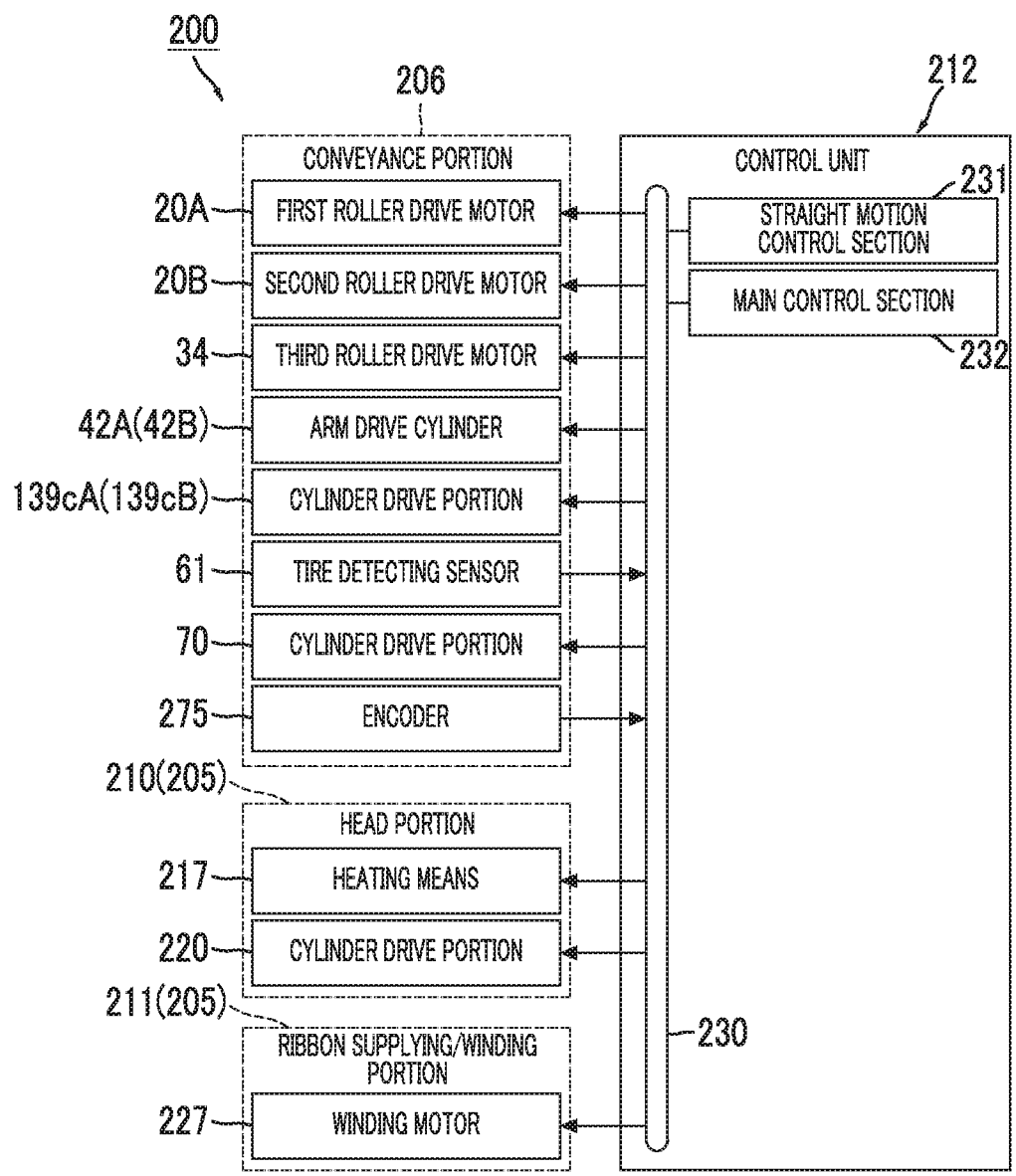
FIG. 7 is a block diagram illustrating a schematic configuration of a tire marking portion of the tire characteristic value measurement apparatus according to the second embodiment of the present invention.

FIG. 6 is a front view illustrating a schematic configuration of a tire marking apparatus of the tire characteristic value measurement apparatus according to the second embodiment of the present invention. FIG. 7 is a block diagram illustrating a schematic configuration of a tire marking portion of the tire characteristic value measurement apparatus according to the second embodiment of the present invention.

The tire marking portion 205 performs marking on the tire T. As illustrated in FIGS. 6 and 7, the tire marking portion 205 includes a head portion 210 and a ribbon supplying/winding portion 211.

The head portion 210 is disposed above the roller conveyor 101 of the conveyance portion 206. The head portion 210 includes marking pins (marking portions) 214, air cylinders 215, and heating means 217.

Each of the marking pins 214 is formed such that a shape such as a circle shape and a triangle shape protrudes from the lower surface thereof. The marking pins 214 are provided so as to be slidable in the upward/downward direction.

The air cylinders 215 are disposed so as to be able to respectively press down the marking pins 214. The marking pins 214 are biased upward and move downward only when being pressed by the air cylinders 215.

The heating means 217 is provided so as to be able to heat the marking pins 214 in accordance with electrification to a heater, and the like.

The ribbon supplying/winding portion 211 is attached to the head portion 210. The ribbon supplying/winding portion 211 includes a ribbon supplying roller 223, a ribbon winding roller 226, and a winding motor 227.

An ink ribbon R is wound around the ribbon supplying roller 223. As the ink ribbon R, it is possible to use a heat transfer-type ribbon which transfers ink by being pressurized and heated.

The ink ribbon R unwound from the ribbon supplying roller 223 is disposed so as to be able to pass through below the head portion 210. The ink ribbon R is disposed at a position facing the lower surfaces of the marking pins 214.

The ribbon winding roller 226 winds the ink ribbon R. The ribbon winding roller 226 turns due to an output of a rotor of the winding motor 227.

According to the tire marking portion 205 described above, when the marking pin 214 is pressed downward by the air cylinder 215, the marking pin 214 moves downward against the biasing force of the marking pin 214 due to the pressing. Accordingly, the lower surface of the marking pin 214 presses the ink ribbon R downward. In this case, the heated marking pin 214 pushes the ink ribbon R against a side wall of the tire T. Accordingly, the ink of the ink ribbon R is transferred to the side wall or the like of the tire T, in a shape such as a circle shape and a triangle shape.

Figure 8:
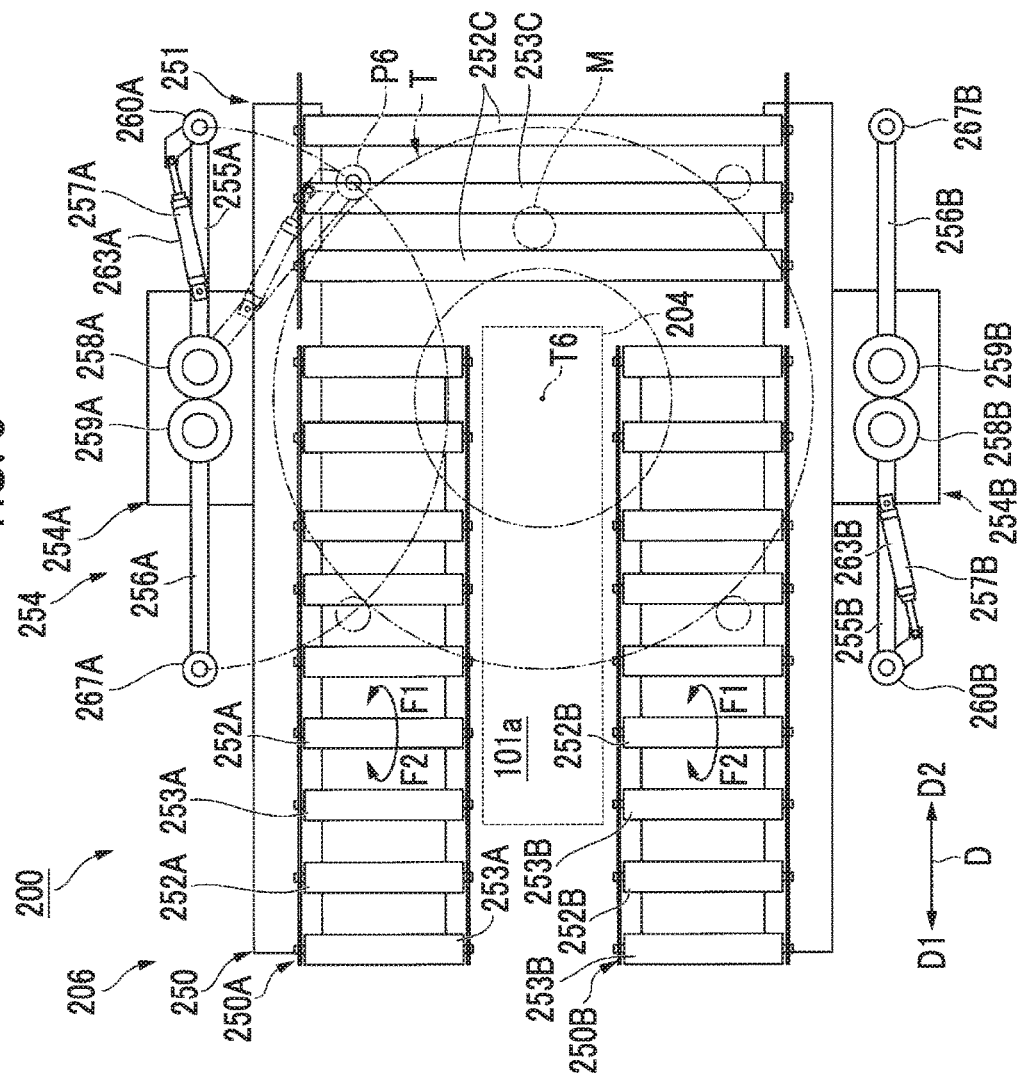
FIG. 8 is a plan view illustrating a schematic configuration of a conveyance portion of the tire characteristic value measurement apparatus according to the second embodiment of the present invention.

FIG. 8 is a plan view illustrating a schematic configuration of a conveyance portion of the tire characteristic value measurement apparatus according to the second embodiment of the present invention.

As illustrated in FIG. 8, the conveyance portion 206 conveys the tire T in the horizontal direction in a state where the tire T conveyed to the weight measurement station 203 is laid. The conveyance portion 206 includes a divided conveyance lane 250, an integrated conveyance lane 251, and a center position adjustment mechanism 254. The divided conveyance lane 250 and the integrated conveyance lane 251 in the second embodiment are so-called roller conveyors.

The divided conveyance lane 250 includes a first conveyance lane 250A and a second conveyance lane 250B. The first conveyance lane 250A and the second conveyance lane 250B are disposed so as to be parallel to each other and be separated from each other in the horizontal direction orthogonal to the conveyance direction. The advance/retreat slit 101a described in the first embodiment is disposed between the first conveyance lane 250A and the second conveyance lane 250B. Through the advance/retreat slit 101a, the support arms 124, the probes 133 and 138, and the like of the weight/electric resistance measurement portion 204 can protrude and retract from below with respect to the conveyance surface of the divided conveyance lane 250.

The first conveyance lane 250A includes first drive rollers 252A and first free rollers 253A. The first drive rollers 252A are driven by a first roller drive motor 20A (refer to FIG. 7). The first free rollers 253A are provided so as to freely rotate. In the first conveyance lane 250A of the second embodiment, the first drive rollers 252A and the first free rollers 253A are alternately disposed in the conveyance direction.

The second conveyance lane 250B has a configuration similar to that of the first conveyance lane 250A and includes second drive rollers 252B and second free rollers 253B. The second drive rollers 252B are driven by a second roller drive motor 20B (refer to FIG. 7). The second free rollers 253B are provided so as to freely rotate. In the second conveyance lane 250B of the second embodiment, the second drive rollers 252B and the second free rollers 253B are alternately disposed in the conveyance direction.

The integrated conveyance lane 251 includes third drive rollers 252C and third free rollers 253C. The third drive rollers 252C are driven by a third roller drive motor 34 (refer to FIG. 7). The third free rollers 253C are provided so as to freely rotate. In the integrated conveyance lane 251 of the second embodiment, the third drive rollers 252C and the third free rollers 253C are alternately disposed in the conveyance direction.

The first free rollers 253A, the second free rollers 253B, and the third free rollers 253C described above abut the side wall of a conveyed tire T on the lower side in an auxiliary manner.

The center position adjustment mechanism 254 moves the tire T such that the center position of the tire T is disposed at a predetermined marking position T6 when marking is performed on the conveyance portion 206 by the tire marking portion 205. Moreover, the center position adjustment mechanism 254 can cause the tire T disposed at the marking position T6 to rotate around the axis line thereof. The center position adjustment mechanism 254 includes a first positioning portion 254A and a second positioning portion 254B. Here, a tire detecting sensor 61 (refer to FIG. 7) is provided in the conveyance portion 206. The tire detecting sensor 61 detects the conveyance position of the tire T and transmits the detection result to a control unit 212.

Here, the tire marking portion 205 described above is disposed at a predetermined position in the tire T disposed at the marking position T6, for example, a position vertically above the side wall on the downstream side. The tire marking portion 205 is formed so as to be able to be lifted and lowered. The tire marking portion 205 is lowered when marking is performed. For example, marking is performed at a position M illustrated in FIG. 8.

The first positioning portion 254A includes a pair of holding arms 255A and 256A and a rotary drive portion 257A.

The holding arms 255A and 256A are disposed on a first side in the width direction of the conveyance portion 206. The holding arm 255A is disposed on the downstream (in FIG. 8, the direction indicated by D2) side of the holding arm 256A. Each of the first end portions (base end portions) of the holding arms 255A and 256A is supported so as to be able to oscillate around the oscillation axis extending in the upward/downward direction. The holding arms 255A and 256A are interlocked with each other via gears 258A and 259A respectively provided in the first end portions (base end portions). Accordingly, the holding arms 255A and 256A respectively and simultaneously oscillate around the first end portions (base end portions) on a plane parallel to the horizontal plane. In this case, the second end portions (tip end portions) of the holding arms 255A and 256A individually move between a storage position which is not disposed in the divided conveyance lane 250 and a position vertically above the integrated conveyance lane 251, and the operation position which is disposed in the divided conveyance lane 250 or a position vertically above the integrated conveyance lane 251. The holding arms 255A and 256A are moved by an arm drive cylinder 42A (refer to FIG. 2) via the gears 258A and 259A.

Figure 9:
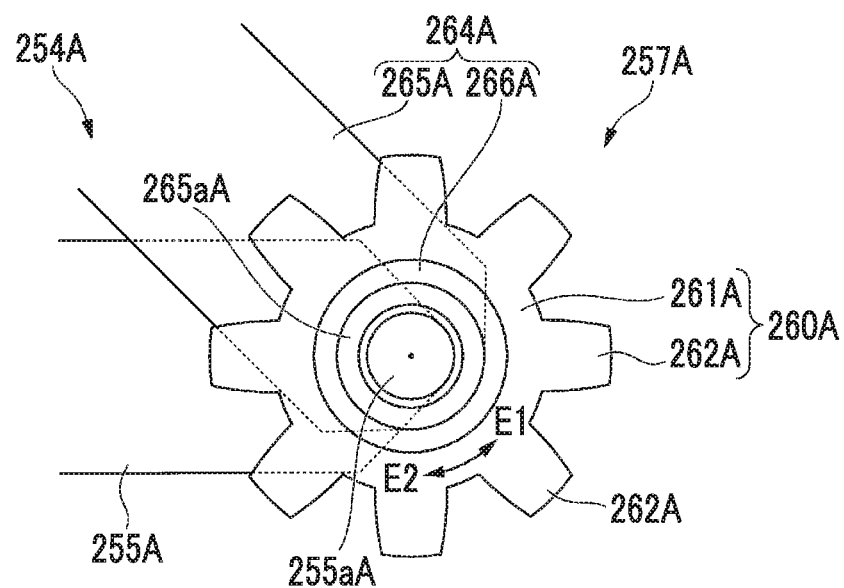
FIG. 9 is a plan view illustrating a schematic configuration of a first positioning portion of the tire characteristic value measurement apparatus according to the second embodiment of the present invention.

FIG. 9 is a plan view illustrating a schematic configuration of a first positioning portion of the tire characteristic value measurement apparatus according to the second embodiment of the present invention.

As illustrated in FIG. 9, the second end portion of the holding arm 255A includes a columnar shaft member 255aA. A drive roller (rotary position adjustment roller, roller) 260A is rotatably supported by the shaft member 255aA. The drive roller 260A is rotatably supported around the axis line orthogonal to the horizontal plane.

Figure 10:
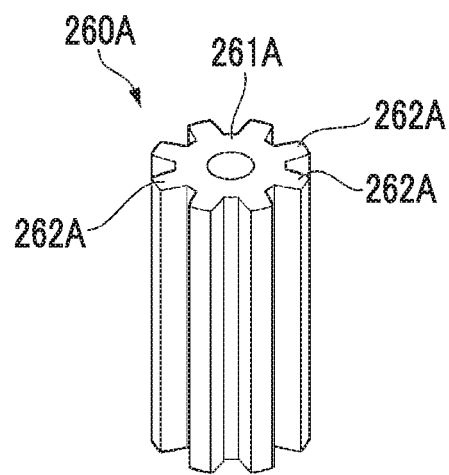
FIG. 10 is a perspective view of a drive roller of the tire characteristic value measurement apparatus according to the second embodiment of the present invention.

FIG. 10 is a perspective view of a drive roller of the tire characteristic value measurement apparatus according to the second embodiment of the present invention.

As illustrated in FIG. 10, the drive roller 260A includes a roller main body 261A and outer projection portions 262A. The roller main body 261A is formed so as to have a cylindrical shape. The outer projection portions 262A are formed so as to protrude from the outer circumferential surface of the roller main body 261A and extend along the axis line of the roller main body 261A. A plurality of the outer projection portions 262A is formed with gaps in the circumferential direction of the roller main body 261A.

Here, the roller main body 261A and the outer projection portions 262A configuring the drive roller 260A can be configured by using a steel timing pulley or can be integrally formed of a resin such as nylon and polyoxymethylene (POM). In addition, the drive roller 260A can be configured not to have the plurality of outer projection portions 262A. In this case, a material of which frictional coefficient becomes significant on the outer circumferential surface of the roller main body 261A may be used for the drive roller 260A.

Figure 11:
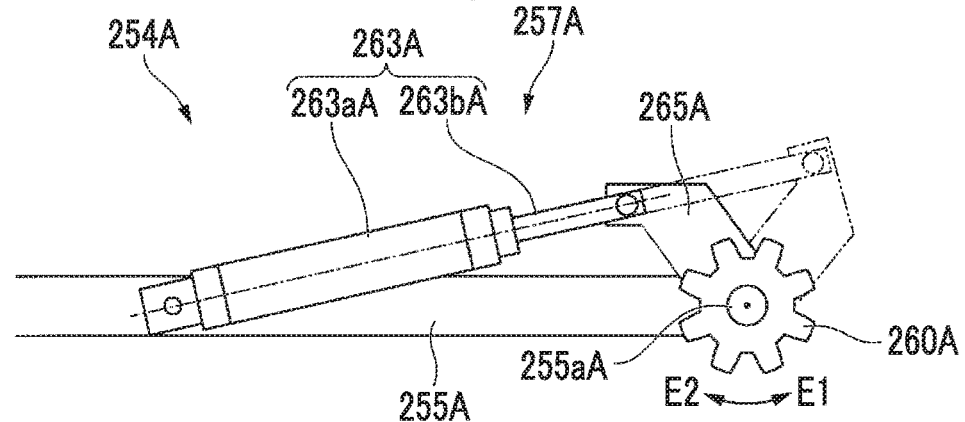
FIG. 11 is a plan view of a holding arm and a rotary drive portion of the tire characteristic value measurement apparatus according to the second embodiment of the present invention.

FIG. 11 is a plan view of a holding arm and a rotary drive portion of the tire characteristic value measurement apparatus according to the second embodiment of the present invention.

As illustrated in FIG. 11, the rotary drive portion 257A is attached to the holding arm 255A. The rotary drive portion 257A rotates the drive roller 260A.

As illustrated in FIGS. 9 and 11, the rotary drive portion 257A includes an air cylinder 263A and a converting portion 264A.

The air cylinder 263A includes an outer tube 263aA and a rod 263bA. In the air cylinder 263A, the rod 263bA can protrude and retract in the longitudinal direction thereof with respect to the outer tube 263aA due to a working fluid supplied from the outside. The description is given with an example of an air cylinder driven by compressed air. However, the air cylinder is not limited to that driven by compressed air as long as the air cylinder has a mechanism which can be driven straight.

As illustrated in FIG. 9, the converting portion 264A includes a link member 265A and a clutch mechanism 266A.

The link member 265A is rotatably connected to the tip end portion of the rod 263bA. The link member 265A has a second end portion 265aA which is formed so as to have a cylindrical shape, on a side opposite to the tip end portion of a rod 263b. In the second end portion 265aA, the shaft member 255aA of the holding arm 255A is rotatably inserted through the inside of a cylindrical hole thereof.

The clutch mechanism 266A is externally fitted to the second end portion 265aA. The roller main body 261A of the drive roller 260A is externally fitted to the clutch mechanism 266A. The clutch mechanism 266A regulates the rotation of the drive roller 260A in a direction (one direction) E1 with respect to the second end portion 265aA. In other words, the clutch mechanism 266A allows the drive roller 260A to rotate in a direction E2 with respect to the second end portion 265aA.

A roller 267A is supported by the second end portion of the holding arm 256A so as to freely rotate. The roller 267A is driven in accordance with the rotation of the tire T in the circumferential direction when abutting the tire T.

As illustrated in FIG. 8, the second positioning portion 254B includes a pair of holding arms 255B and 256B and a rotary drive portion 257B. The holding arms 255B and 256B are disposed on a second side in the width direction of the conveyance portion 206. The holding arm 255B is disposed on an upstream side D1 of the holding arm 256B. The holding arm 255B and the holding arm 256B are interlocked with each other via gears 258B and 259B.

The second positioning portion 254B has a configuration similar to that of the first positioning portion 254A and is disposed on a side opposite to the first positioning portion 254A, while interposing the conveyance portion 206 therebetween.

Here, the configuration of the rotary drive portion 257B is similar to the configuration of the rotary drive portion 257A, except the disposition thereof. Therefore, the detailed description will be omitted. In FIG. 8, a reference sign in which the postfix "A" of the reference sign applied to each of the configuration of the rotary drive portion 257A is replaced by "B" is applied to each of the configuration of the rotary drive portion 257B corresponding to each of the configuration of the rotary drive portion 257A.

Figure 12:
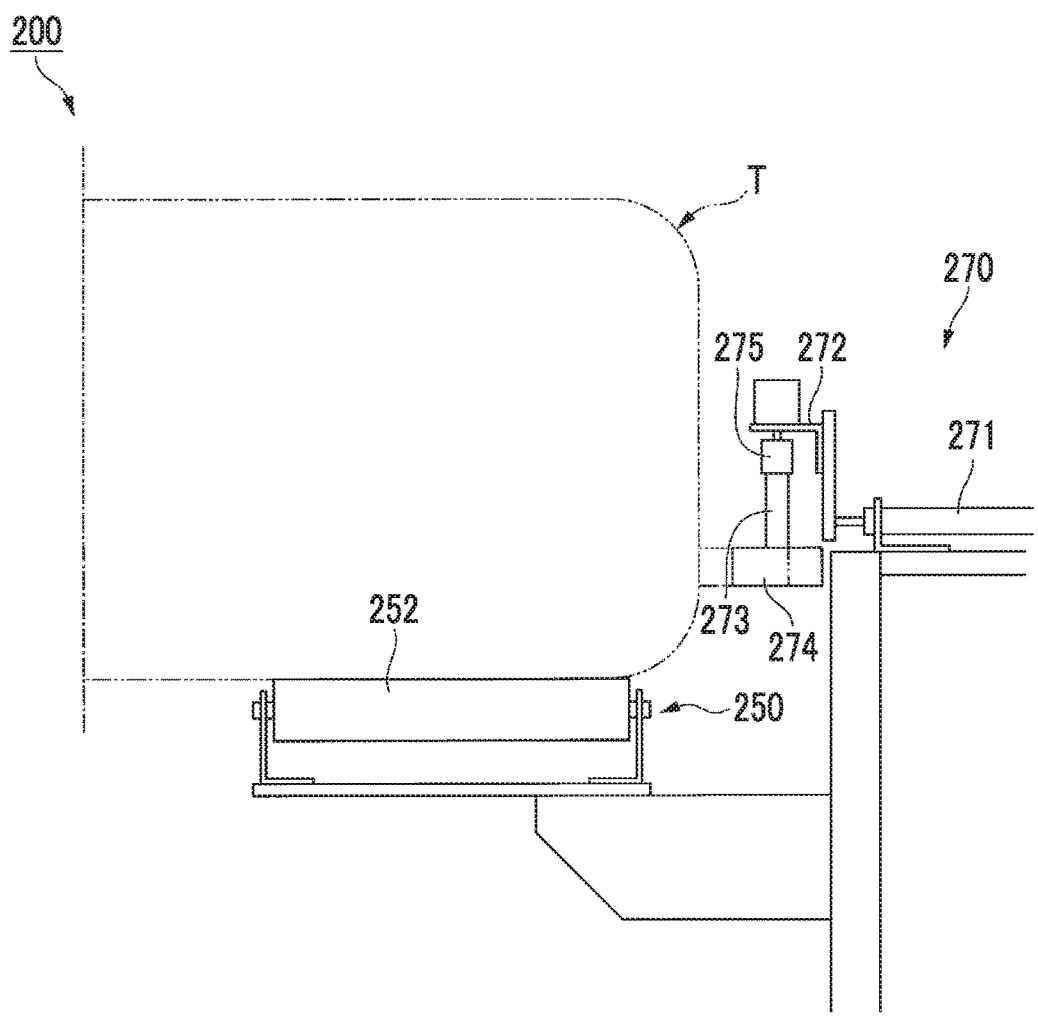
FIG. 12 is a front view illustrating a schematic configuration of a rotation amount detection portion of the tire characteristic value measurement apparatus according to the second embodiment of the present invention.

FIG. 12 is a front view illustrating a schematic configuration of a rotation amount detection portion of the tire characteristic value measurement apparatus according to the second embodiment of the present invention.

As illustrated in FIG. 12, the conveyance portion 206 is provided with a rotation amount detection portion 270. The rotation amount detection portion 270 detects the rotation amount of the tire T rotated by the center position adjustment mechanism 254. The rotation amount detection portion 270 includes an air cylinder 271, a coupling member 272, a rotary shaft 273, a detection roller 274, and an encoder 275.

The air cylinder 271 causes the coupling member 272 to approach and be separated from the tread of the tire T in the radial direction of the tire T. The air cylinder 271 is driven by a cylinder drive portion 70 (refer to FIG. 7).

The coupling member 272 supports the rotary shaft 273 in a manner of freely rotating around the axis line parallel to the central axis of the tire T.

The detection roller 274 is fixed to the end portion of the rotary shaft 273. The detection roller 274 is formed so as to have a columnar shape having a diameter greater than the rotary shaft 273. The outer circumferential surface of the detection roller 274 comes into contact with the tread of the tire T when the coupling member 272 approaches the tire T due to the air cylinder 271. In addition, the outer circumferential surface of the detection roller 274 is separated from the tread of the tire T when the coupling member 272 is separated from the tire T due to the air cylinder 271.

The encoder 275 detects the rotation amount of the rotary shaft 273, that is, the rotation amount of the detection roller 274. In other words, when the detection roller 274 approaches the tread of the tire T, the encoder 275 can detect the rotation amount of the tire T around the central axis. The detection result of the encoder 275 is transmitted to the control unit 212 described below.

As illustrated in FIG. 7, the control unit 212 has a direct motion control section 231 and a main control section 232 connected to a bus 230.

Each of the direct motion control section 231 and the main control section 232 is configured to have a timer, a calculation element, a memory, a control program, and the like.

The direct motion control section 231 controls air cylinders 139A and 139B by driving cylinder drive portions 139cA and 139cB, based on the detection result of the encoder 275.

The main control section 232 controls devices other than the cylinder drive portions 139cA and 139cB connected to the bus 230.

The first roller drive motor 20A, the second roller drive motor 20B, the third roller drive motor 34, the arm drive cylinders 42A and 42B, the cylinder drive portions 139cA, 139cB, and 70, the tire detecting sensor 61, the encoder 275, the heating means 217 of the head portion 210, a cylinder drive portion 220, and the winding motor 227 of the ribbon supplying/winding portion 211 are connected to the bus 230. Moreover, the output portion 201b of the tire uniformity machine 201, and the output portion 202b of the dynamic balancing machine 202 are connected to the bus 230.

The tire characteristic value measurement apparatus 200 of the second embodiment has the configuration described above. Subsequently, an operation of the tire characteristic value measurement apparatus 200 will be described.

First, the tire uniformity machine 201 and the dynamic balancing machine 202 measure the tire T (measurement target). Thereafter, the tire T is carried into the weight measurement station 203 by the conveyance portion 206.

When the tire T is carried into the weight measurement station 203, the control unit 212 causes the conveyance portion 206 to convey the tire T to the divided conveyance lane 250. Similar to the first embodiment, the weight and the electric resistance of the tire T are measured in a state where the tire T is supported by the support arms 124 from below and is separated from the divided conveyance lane 250.

Subsequently, the control unit 212 causes the support arms 124 to move downward such that the tire T is placed on the divided conveyance lane 250 of the conveyance portion 206. Here, the tire T is disposed in a state where the position in the circumferential direction in which marking is performed when the tire T is carried in is adjusted. The position of the circumferential direction does not change even after the weight and the electric resistance are measured.

The control unit 212 controls the cylinder drive portions 139cA and 139cB such that the central axis of the tire T is positioned on the marking position T6 set in advance, by the center position adjustment mechanism 254. At this time, information such as the outer diameter of the tire T, and the shape, color, and the like of marking performed with respect to the tire T is transmitted to the control unit 212 from the tire uniformity machine 201 and the dynamic balancing machine 202.

For example, the control unit 212 performs first marking based on the measurement result of the tire uniformity machine 201. The control unit 212 causes the marking pin 214, which is heated in advance by driving the cylinder drive portion 220, to protrude downward. Accordingly, the first marking is performed by using the ink of the ink ribbon R with respect to the side wall oriented to the upper side of the tire T.

Subsequently, for example, the control unit 212 performs second marking based on the measurement result of the dynamic balancing machine 202. In this case, the control unit 212 drives the cylinder drive portions 139cA and 139cB such that the drive rollers 260A and 260B are inching-driven. The tire T is rotated in the circumferential direction through the inching-driving, and the position of performing the second marking is disposed at a position where marking can be performed by using the marking pin 214.

Here, the inching-driving is an operation in which the drive roller 260A repetitively rotates by a uniform rotary angle. When the rod 263bA protrudes and retracts, the drive roller 260A rotates by a uniform rotary angle around an axis line 38bA. The control unit 212 performs the inching-driving by repeating the protruding and retracting a predetermined number of times while having the protruding and retracting of the rods 263bA and 263bB of the air cylinders 263A and 263B as one set.

When the inching-driving is performed, the control unit 212 drives the cylinder drive portion 70 such that the side surface of the detection roller 274 abuts the tread of the tire T. Accordingly, the rotation amount of the tire T through the inching-driving is detected by the encoder 275. The control unit 212 continues the inching-driving based on the detection result obtained by the encoder 275, until the rotation amount of the tire T reaches a target rotation amount, that is, until the position of the second marking for the tire T reaches a position where marking can be performed by using the marking pin 214.

Thereafter, the control unit 212 drives the cylinder drive portion 220 such that the marking pin 214 protrudes. Accordingly, the ink of the ink ribbon R is transferred to the side wall of the tire T as the second marking.

The description is given regarding a case where the second marking is performed after the first marking. However, the additional marking may be performed at a position different from the first marking and second marking by rotating the tire T in the circumferential direction through the inching-driving after the second marking is performed.

Subsequently, the control unit 212 drives the cylinder drive portion 70 such that the detection roller 274 is separated from the tread of the tire T. Moreover, the control unit 212 drives the arm drive cylinders 42A and 42B such that the drive roller 260A, the roller 267A, the drive roller 260B, and a roller 267B are individually separated from the tread of the tire T.

Thereafter, the control unit 212 causes the conveyance portion 206 to convey the tire T toward the downstream side D2 such that the tire T is carried out from the weight measurement station 203.

According to the second embodiment, the tire T can be rotated in the circumferential direction by having the drive rollers 260A and 260B and the rotary drive portions 257A and 257B. When the tire T is rotated in the circumferential direction, the positions in the tire T in the circumferential direction where marking is performed by using the marking pins 214 can be different from each other.

Accordingly, according to the simple configuration using the center position adjustment mechanism 254 adjusting the center position of the tire T, a plurality types of marking different from each other can be performed by rotating the tire T with respect to the marking pins 214.

Moreover, when the outer projection portions 262A are formed in the drive roller 260A, the frictional force between the drive roller 260A and the tire T can be enhanced.

In addition, by providing the weight/electric resistance measurement portion 204 and the tire marking portion 205 in the weight measurement station 203, marking is performed by the tire marking portion 205 with respect to the tire T based on the measurement results of the tire uniformity machine 201 and the dynamic balancing machine 202.

Therefore, compared to a case where a tire marking apparatus for the tire uniformity machine 201 and a tire marking apparatus for the dynamic balancing machine 202 are separately provided, the overall length of a tire characteristic value measurement system can be shortened. In addition, since two or more types of marking can be performed without conveying the tire T, it is possible to shorten the time taken to perform two or more types of marking.

Moreover, the tire marking portion 205 is disposed above the weight/electric resistance measurement portion 204. Therefore, compared to a case and the like where the weight/electric resistance measurement portion 204 and the tire marking apparatus are provided in separate stations, the overall length of the tire characteristic value measurement system can be further shortened.

This invention is not limited to the configuration of each of the embodiments described above, and the design can be changed within a range of not departing from the gist thereof.

For example, in the second embodiment described above, description is given regarding a case where the tire T is rotated by the center position adjustment mechanism 254. However, the tire marking portion 205 may be moved in the circumferential direction along the side wall oriented toward the upper side of the tire T. In this case, the mechanism for the inching-driving performed by the center position adjustment mechanism 254 can be omitted.

In addition, in the second embodiment described above, description is given regarding a case where the ink ribbon R is provided and marking is performed by using the marking pin 214 corresponding to the ink ribbon R. However, the numbers of the ink ribbons and the marking pins 214 are not limited to the number and the quantity described above. Two or more ink ribbons may be used.

Moreover, in the second embodiment, description is given regarding a case where marking is performed by using the ink ribbon R. However, the tire marking portion 205 is acceptable as long as marking can be performed with respect to the tire T, and a tire marking portion not using the ink ribbon R may be used.

In addition, in the second embodiment described above, description is given regarding a case where marking is performed with respect to the tire T after the weight and the electric resistance of the tire T are measured. However, the timing for performing marking is not limited to the time after the weight and the electric resistance are measured. For example, the marking may be performed before the weight and the electric resistance are performed.

Moreover, in the center position adjustment mechanism 254 of the second embodiment described above, description is given regarding a case where the drive rollers 260A and 260B are respectively rotated by the air cylinders 263A and 263B. However, the mechanism of rotating the drive rollers 260A and 260B is not limited to the air cylinders 263A and 263B.

In addition, in the second embodiment, description is given regarding an example of a case where the dynamic balancing machine 202 is disposed a downstream side of the tire uniformity machine 201 in the conveyance direction of the tire T. However, disposition of the tire uniformity machine 201 and the dynamic balancing machine 202 is not limited to the disposition described above.

INDUSTRIAL APPLICABILITY

According to a tire characteristic value measurement apparatus of the present invention, measuring an electric resistance value of a tire can be easily executed with high accuracy. Therefore, the tire characteristic value measurement apparatus can be utilized in the tire manufacturing industry in a highly useful manner.

REFERENCE SIGNS LIST

10 FLOOR SURFACE
11 MAIN BODY FRAME
20A FIRST ROLLER DRIVE MOTOR
20B SECOND ROLLER DRIVE MOTOR
34 THIRD ROLLER DRIVE MOTOR
42A, 42B ARM DRIVE CYLINDER
61 TIRE DETECTING SENSOR
70 CYLINDER DRIVE PORTION
100 TIRE CHARACTERISTIC VALUE MEASUREMENT APPARATUS
101 ROLLER CONVEYOR
101a ADVANCE/RETREAT SLIT
111 COLUMN
112 GUIDE RAIL
113 SLIDER
114 ATTACHMENT PLATE
115 BRACKET
116 COUPLING PLATE
117 AIR CYLINDER
118 ATTACHMENT PLATE
119 SUPPORT PLATE
120 BRACKET
121 SUPPORT TABLE
122 LOAD CELL
123 SUPPORT FRAME
124 SUPPORT ARM
125 STRUT

126 BRACKET
127 BASE PLATE
128 FRAME BODY
129 GUIDE ROD
130 SLIDE BLOCK
131 COUPLING PLATE
132 SUPPORT MEMBER
133 PROBE
134 SLIDE BLOCK
135 COUPLING PLATE
136 SUPPORT MEMBER
137a VERTICAL FRAME
137b TRANSVERSE FRAME
138 PROBE
139 AIR CYLINDER
139a OUTER TUBE
139b INNER ROD
140 CALCULATION CONTROL DEVICE
141 DISPLAY
200 TIRE CHARACTERISTIC VALUE MEASUREMENT APPARATUS
201 TIRE UNIFORMITY MACHINE
201a MEASUREMENT PORTION
201b OUTPUT PORTION
202 DYNAMIC BALANCING MACHINE
202a MEASUREMENT PORTION
202b OUTPUT PORTION
203 WEIGHT MEASUREMENT STATION
204 WEIGHT/ELECTRIC RESISTANCE MEASUREMENT PORTION
205 TIRE MARKING PORTION
206 CONVEYANCE PORTION
210 HEAD PORTION
211 RIBBON SUPPLYING/WINDING PORTION
212 CONTROL UNIT
214 MARKING PIN
215 AIR CYLINDER
217 HEATING MEANS
220 CYLINDER DRIVE PORTION
223 RIBBON SUPPLYING ROLLER
226 RIBBON WINDING ROLLER
227 WINDING MOTOR
230 BUS
231 DIRECT MOTION CONTROL SECTION
232 MAIN CONTROL SECTION
250 DIVIDED CONVEYANCE LANE
250A FIRST CONVEYANCE LANE
250B SECOND CONVEYANCE LANE
251 INTEGRATED CONVEYANCE LANE
252A FIRST DRIVE ROLLER
253A FIRST FREE ROLLER
252B SECOND DRIVE ROLLER
253B SECOND FREE ROLLER
252C THIRD DRIVE ROLLER
253C THIRD FREE ROLLER
254 CENTER POSITION ADJUSTMENT MECHANISM
254A FIRST POSITIONING PORTION
254B SECOND POSITIONING PORTION
255A, 256A HOLDING ARM
255B, 256B HOLDING ARM
255aA SHAFT MEMBER
257A ROTARY DRIVE PORTION
258A, 259A GEAR
258B, 259B GEAR
260A, 260B DRIVE ROLLER
261A, 261B ROLLER MAIN BODY
262A, 262B OUTER PROJECTION PORTION
263A, 263B AIR CYLINDER
263aA OUTER TUBE
263bA ROD
264A CONVERTING PORTION
265A LINK MEMBER
265aA SECOND END PORTION
266A CLUTCH MECHANISM
267A ROLLER
270 ROTATION AMOUNT DETECTION PORTION
271 AIR CYLINDER
272 COUPLING MEMBER
273 ROTARY SHAFT
274 DETECTION ROLLER
275 ENCODER
T TIRE

The invention claimed is:

1. A tire characteristic value measurement apparatus comprising:
conveyance means for conveying a tire;
vertical movement means which is disposed below the conveyance means and is able to vertically move;
a bearing member which is provided in the vertical movement means and bears the tire on the conveyance means from below in accordance with a rise, and in which at least a contact surface to be brought into contact with the tire has electrically insulative properties; and
electric resistance value detection means which is provided in the vertical movement means and detects an electric resistance value of the tire borne by the bearing member.

2. The tire characteristic value measurement apparatus according to claim 1, further comprising:
weight detection means which is provided in the vertical movement means and detects a weight of the tire borne by the bearing member.

3. The tire characteristic value measurement apparatus according to claim 2,
wherein the vertical movement means includes
a fluid pressure cylinder which is installed such that an axial direction is oriented toward an upward/downward direction,
an offset support member of which a base end portion is coupled to an upper end of the fluid pressure cylinder and of which a tip end portion is positioned at a position offset to the side lower than the upper end of the fluid pressure cylinder when the fluid pressure cylinder contracts, and
guide means which is coupled to the offset support member and guides a vertical movement of the offset support member,
wherein the weight detection means and the electric resistance value detection means are supported by the tip end portion of the offset support member of the vertical movement means, and
wherein the bearing member is provided in the weight detection means.

4. The tire characteristic value measurement apparatus according to claim 3,
wherein the guide means of the vertical movement means includes
a pair of guide rails of which a longitudinal direction is oriented toward the upward/downward direction, and
sliders which are respectively provided in the guide rails so as to be able to slide along the longitudinal direction of the guide rails and are individually coupled to the offset support member.

5. The tire characteristic value measurement apparatus according to claim 3,
wherein the electric resistance value detection means includes
probes which make a pair, and
probe holding means which is supported by the tip end portion of the offset support member of the vertical movement means and holds the probes making a pair such that the probes are able to move in a direction of approaching and being separated from each other.

6. The tire characteristic value measurement apparatus according to claim 2, further comprising:
a weight measurement station which has a weight/electric resistance measurement portion having the electric resistance value detection means and the weight detection means, and a tire marking portion being able to perform marking on the tire, and in which the tire marking portion is disposed above the weight/electric resistance measurement portion.

7. The tire characteristic value measurement apparatus according to claim 6,
wherein the weight measurement station includes a center position adjustment mechanism which adjusts a center position of the tire, and
wherein the center position adjustment mechanism includes a rotary position adjustment roller which abuts a part of the tire and is rotated so as to rotate the tire around an axis line of the tire.

8. A tire characteristic value measurement system comprising:
the tire characteristic value measurement apparatus according to claim 6;
a uniformity machine which is disposed on an upstream side of the weight measurement station in a conveyance direction of the tire and measures uniformity of the tire; and
a dynamic balancing machine which is disposed on an upstream side of the weight measurement station in the conveyance direction of the tire and measures an amount of imbalance in the tire,
wherein the tire marking portion individually marks a measurement result of the uniformity machine and a measurement result of the dynamic balancing machine on the tire.

* * * * *